(12) United States Patent
Lamm

(10) Patent No.: US 7,264,595 B2
(45) Date of Patent: Sep. 4, 2007

(54) METHOD FOR DETECTION AND IMPROVING VISUAL ATTENTION DEFICIT IN HUMANS AND SYSTEM FOR IMPLEMENTATION OF THIS METHOD

(75) Inventor: Oren Lamm, Haifa (IL)

(73) Assignee: Disyvisi Ltd., Haifa Bay (IL)

( * ) Notice: Subject to any disclaimer, the term of this patent is extended or adjusted under 35 U.S.C. 154(b) by 272 days.

(21) Appl. No.: 10/772,415

(22) Filed: Feb. 6, 2004

(65) Prior Publication Data

US 2005/0024588 A1    Feb. 3, 2005

Related U.S. Application Data

(60) Provisional application No. 60/445,266, filed on Feb. 6, 2003.

(51) Int. Cl.
*A61B 13/00* (2006.01)
(52) U.S. Cl. .................................................... 600/558
(58) Field of Classification Search ................ 600/558, 600/27, 300
See application file for complete search history.

(56) References Cited

U.S. PATENT DOCUMENTS

| 4,162,493 A * | 7/1979 | Ross et al. ..................... 345/59 |
| 2004/0049124 A1* | 3/2004 | Kullok et al. ................ 600/558 |

* cited by examiner

*Primary Examiner*—Max Hindenburg
*Assistant Examiner*—H. Q. Nguyen
(74) *Attorney, Agent, or Firm*—Blank Rome LLP

(57) ABSTRACT

Method and system for detection and treatment of visual attention deficit is suggested. The method is based on exposing a patient to a visual display, capable to generate various images suitable for use as stimuli and to run the stimuli with a required frequency in front of the patient. Following the training program, the patient's performance becomes considerably improved both in terms of display test and in daily reading tasks.

19 Claims, 4 Drawing Sheets

Fig.2 Stimuli used at training step

| | | |
|---|---|---|
| 1. | A point - (נקודה). | |
| 2. | Hebrew letter - ר | |
| 3. | Hebrew letter - כ | |
| 4. | Hebrew letter - ם | |
| 5. | Hebrew letter - נ | |
| 6. | Hebrew letter - ב | |
| 7. | Hebrew letter - ד | |
| 8. | Hebrew letter -- ש | |
| 9. | Hebrew letter - פ | |
| 10. | Hebrew letter - צ | |
| 11. | Hebrew letter - ל | |
| 12. | Camel - גמל | |
| 13. | Book - ספר | |
| 14. | Door - דלת | |
| 15. | 3, 5, 8 | |

Fig.3a Stimuli used at diagnostic and treatment step

List 1

1. Wheel - גלגל
2. Watch - שעון
3. Window - חלון
4. Train - רכבת
5. Work - עבודה
6. Plants - צמחים

List 2

1. Big - גדול
2. Test - מבחן
3. Good bye - שלום
4. Computer - מחשב
5. Clinic - מרפאה
6. Paves/Ways/ trails - שבילים

Fig.3b Stimuli used at diagnostic and treatment step (continuation)

<u>List 3</u>

| | | |
|---:|---:|---:|
| 1. | Finished - גמור |
| 2. | Week - שבוע |
| 3. | Written - כתוב |
| 4. | Comb - מסרק |
| 5. | Thinking - חשיבה |
| 6. | Workers - פועלים |

<u>List 4</u>

| | | |
|---:|---:|---:|
| 1. | Police - משטרה |
| 2. | Tears - דמעות |
| 3. | Button - כפתור |
| 4. | Broom - מטאטא |
| 5. | Judges - שופטים |
| 6. | Prisoner - שבויה |

<u>List 5</u>

| | | |
|---:|---:|---:|
| 1. | Camera - מצלמה |
| 2. | Cards - קלפים |
| 3. | Brigade - פלוגה |
| 4. | Guarding - שמירה |
| 5. | Sweets - ממתקים |
| 6. | Wild - פרועה |

<u>List 6</u>

| | | |
|---:|---:|---:|
| 1. | Spring board – מקפצה |
| 2. | Details - פרטים |
| 3. | Recording - הקלטה |
| 4. | Control - שליטה |
| 5. | Chocolate - שוקולד |
| 6. | Invasion - פלישה |

Fig.3c Stimuli used at diagnostic and treatment step (continuation)

<u>List 7</u>

| | | |
|---:|---:|---:|
| 1. | clinic - מרפאה | |
| 2. | workers - פועלים | |
| 3. | button- כפתור | |
| 4. | chocolate - שוקולד | |
| 5. | big /large – גדול | |
| 6. | wheel – גלגל | |

<u>List 8</u>

| | |
|---:|---:|
| 1. | judges - שופטים |
| 2. | work - עבודה |
| 3. | cards - קלפים |
| 4. | test - מבחן |
| 5. | broomstick - מטאטא |
| 6. | clock - שעון |

<u>List 9</u>

| | |
|---:|---:|
| 1. | plants - צמחים |
| 2. | week- שבוע |
| 3. | spring board - מקפצה |
| 4. | window - חלון |
| 5. | recording - הקלטה |
| 6. | company - פלוגה |

METHOD FOR DETECTION AND IMPROVING VISUAL ATTENTION DEFICIT IN HUMANS AND SYSTEM FOR IMPLEMENTATION OF THIS METHOD

This application claims priority to PCT/IL04/000097 filed Feb. 6, 2004, and U.S. Provisional Ser. No. 60/445,266 filed Feb. 6, 2003.

BACKGROUND OF THE INVENTION

1. Field of the Invention

The present invention relates to detection and treatment of various temporal integration disorders, affecting certain daily tasks like reading accuracy. More particularly, the present invention concerns estimation of visual attention as opposed to visible persistence and improvement of visual attention in general and reading ability of dyslexic and hyperactive children in particular.

2. Description of the Related Art

Some researches suggest that disorders of reading acquisition in children are related to magnocellular deficit or developmental impediment, see for example U.S. Pat. No. 6,045,515. This hypothesis is supported to some extent by findings that indicate that dyslexics have anomalies in their magnocellular networks, demonstrated by (1) higher contrast thresholds to detect brief patterns, (2) an impaired ability to discriminate both the direction and the velocity of moving patterns, and (3) unstable binocular control and depth localization when compared to normal individuals of the same age. However it should be kept in mind that most of the mentioned evidences were criticized on several grounds by other dyslexia researchers (for review see Hugban 2001).

However, a recent study (Tallal & Merznich 1998) questions whether dyslexic children show a temporal processing deficit, and another study (DeLolo 1996) concludes that the contrast sensitivity functions (CSFs) of dyslexic children are unrelated to their reading ability.

The main claim of those researchers holding the view that dyslexia is related to magnocellular deficit is that dyslexics have longer then normal visible persistence while reading. This assumed to result from the lack of magnocellular inhibitory effect on parvocellular activation. According to this view, the saccadic eye movements between fixations activate, in normal readers, the magnocellular system, which, in turn, suppresses the parvocellular activation initiated by the processing of the text seen at the former fixation.

Due to magnocellular deficit in dyslexics, this inhibitory process is not reliably activated by the short saccades typical in text reading. Thus the transition from eye fixation to the next is accompanied by a masking effect, i.e. visual information gained in a former fixation masks the information gathered in the next or vice versa.

If this assumption was true then watching a text presented on a special display that gives an advantage to longer then normal visible persistence duration could be used to improve dyslexics reading.

Experiments conducted by the inventor with such a display clearly indicated that dyslexics exhibit inferior rather then superior reading of the display texts compared to normal readers. It was also verified that dyslexics were inferior compared to controls in recognition of any stimuli presented by this display. Further investigations indicated that dyslexics' difficulties are related to visual attention deficit that impedes temporal integration of the visual partial signals when they are presented at low frequencies.

BRIEF SUMMARY OF THE INVENTION

In view of the foregoing drawbacks of the methods, known in the art, one of the objectives of the present invention is to provide a method and a system for diagnosis and remediation of reading disorders by respectively measuring and improving visual attention. Exposing the patients to slow smooth pursuit tracking of fragmented stimuli does this.

Dyslexic children who were treated by the method of the present invention significantly decreased their error reading rate after six to eight training hours and became significantly more efficient readers than children treated by other methods.

According to one aspect of the invention, a sequence of alphanumeric stimuli is displayed on a special display, capable to present the stimuli in a running mode. An example of a suitable display is the graphic display system described in the U.S. Pat. No. 4,162,493. In this system the lights of an array are arranged in dot matrix and, when illuminated, are capable to produce the illusion of a moving sign, which is suitable for emulating letters, words, numbers, texts etc. This system has been initially designed for advertising and it employs the phenomenon of beta apparent motion to enable a moving image of a high resolution to be produced with the use of a small proportion for example ⅛, of the number of individual lights that would normally be considered necessary.

The lights are preferably arranged in consecutive columns being illuminated in turn in the direction of apparent movement of the image.

The display system enables controlling of time gaps between stimulus fragments with 1 millisecond precision. It has been empirically revealed that in a large subgroup of poor readers, being exposed to this display a visual attention deficit can be reliably established and this deficit is closely related to their reading difficulties. It has been also found, that the visual attention deficit can be eliminated by further exposing the poor readers to the display according to the method of the present invention, which is described in more details later.

The principle of the present method will be referred-to further as a smooth pursuit tracking of stimuli fragments at slow tracking velocity. Smooth pursuit tracking as opposed to saccadic scanning implies in this context that stimuli should be presented in such a manner that the visual illusion could be generated only if eye movements along the display are continuous and bear no fixations. Slow velocities in this context mean that the time intervals (gaps) between lighted columns are longer than those, which are within the time range of visible persistence limit.

The present invention comprises the following main steps, which are presented in an example below.

Step 1. Preliminary Training of a Patient (Child or Adult).

This step is carried out by exposing a subject to a group of running stimuli consisting of 15 alphanumeric signs and words. The stimuli are displayed by the above mentioned graphic display system in a running mode with a velocity well within human visible persistence range. In practice the required velocity at this step is established by setting a time gap of 80 milliseconds between consecutive display columns. Usually, patients identify the displayed stimuli during the first or second run of the preliminary training step.

Step 2. Diagnostic Setup.

During this step the tested person who passed the first step is exposed to nine word groups each consisted of six words. The groups are displayed at three different velocities, which correspond to the time gaps of 80, 144 and 180 milliseconds. All in all 18 words are presented in each velocity of which six are presented in all velocities. During each run the performance of the subject is recorded in terms of words correctly recognized from each group and at each velocity. On the basis of these results, the subject is attributed either to those who suffer visual attention deficit or not.

Step 3. Treatment Step.

During this step those who suffer visual attention deficit are exposed to alphanumeric symbols and words at an intermediate velocity, which lies between the failure velocity and his last successful velocity. The performance at the intermediate velocity is monitored and the intermediate velocity is varied according to the achieved results.

The present invention refers also to a system, which enables to carry out the above steps. The system comprises visual display connected to a computer, e.g. a PC. The display employed in the system is capable to generate visually recognizable stimuli and to present them in a running mode. The PC employed in the system is provided with suitable software, which enables to control the display, to generate different stimuli, to vary the parameters of their display in the running mode, e.g. time gap between the stimuli, size of stimuli, etc.

The PC is also capable to accumulate, to store, to process the achieved results and to present them statistically, graphically or in any other desirable way, suitable for analysis and monitoring of the results.

BRIEF DESCRIPTION OF THE DRAWINGS

For better understanding of the invention and the way of how it may be carried out in practice, the invention will be now described with reference to the accompanying drawings in which:

FIGS. 2-3 shows various groups of stimuli, which are used for carrying out the method of the invention.

DETAILED DESCRIPTION OF THE INVENTION

Figure 1:
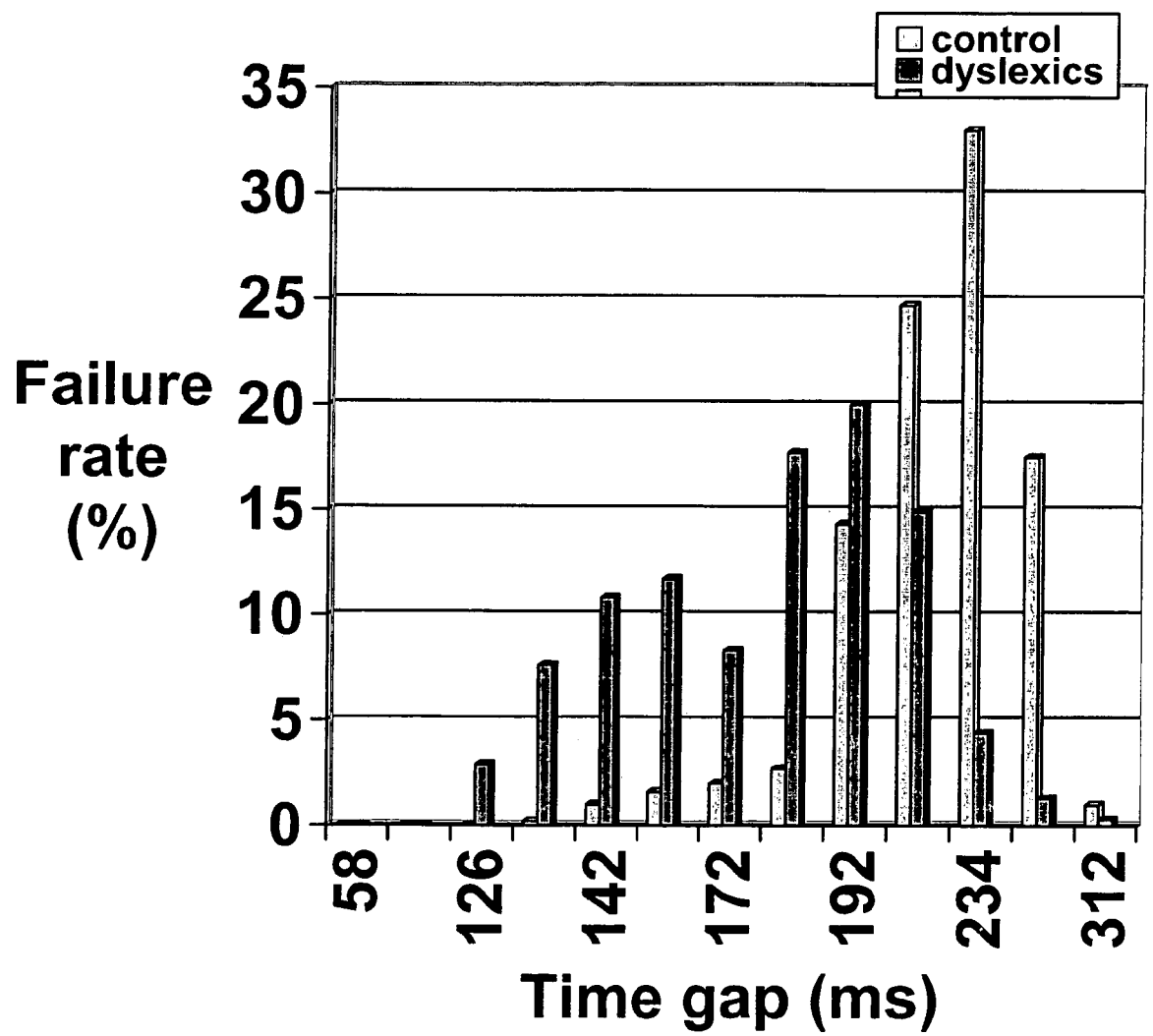
FIG. 1 presents graphically the relation of display velocity to stimuli recognition. The graph refers to a group of dyslexics and a group of control subjects.

The method of the invention has been devised on the basis of empirical work carried out by the Inventor.

The first investigation of the above-mentioned graphic display was intended to test the magnocellular hypothesis. It was hypothesized that dyslexics suffering longer then normal visible persistence would better recognize simple alphanumeric stimuli than normal readers and other dyslexics given that stimuli are presented at low velocities preventing temporal integration on basis of normal visible persistence. However it was found that as much as 30% of the dyslexics were significantly inferior to other dyslexics and normal readers in identifying the presented stimuli running at low velocities.

It was also found that reading training with the aim of the display improves the performance of those who failed both in identification of stimuli at low velocities and in regular text reading—especially with respect to reading error rate. However the early experiments included a small number of subjects (at most 12 subjects in each experimental group) and did not allow a reliable estimation of reading impaired rate and the rate of such subjects that may benefit from a rehabilitation program intended to improve their attentive visual scanning.

Based on the knowledge and data gained from the above-mentioned experiments new large-scale trials were performed. These trials will be described in details since they are the main factual basis for my invention.

EXPERIMENT 1

This experiment was intended to examine the distribution of poor readers, age matched controls and reading age controls according to their performance depending on different presentation velocities.

Method:

Subjects: 551 good readers and 315 poor readers (age range 8 to 55) took part in this experiment. All subjects were native Hebrew speakers that were educated in Israel with normal or corrected visual acuity.

The vocal reading fluency (reading speed and error rate) of all subjects was estimated by normative to age/education level texts. The poor readers sample included only subjects that were 1.5 SD or below normal level on one measure and 1.0 SD or below that on the other. The control sample included only subjects that were at least 0.5 SD above the level on both measures.

Table 1 presents the distribution of subjects in both samples according to their age and gender.

TABLE 1

Subjects' distribution according to age and gender

| | Sums | Females | Males | Age Group |
|---|---|---|---|---|
| | Control group | | | |
| | 188 | 71 | 117 | 12-8 |
| | 168 | 64 | 104 | 17-13 |
| | 154 | 73 | 81 | 25-18 |
| | 41 | 15 | 26 | 55-26 |
| Sums | 551 | 223 | 328 | |
| | Poor readers | | | |
| | 136 | 38 | 98 | 12-8 |
| | 111 | 24 | 87 | 17-13 |
| | 68 | 17 | 51 | 25-18 |
| | — | — | — | 55-25 |
| Sums | 315 | 79 | 236 | |

Procedure

Subjects' competence in identifying fragmented alphanumeric symbols and words in different time gaps between fragments were tested by exposing the subjects to the stimuli running over a graphic display similar to that described in Ross et al. 1976 invention and according to the following procedure:

a) Subjects were instructed to follow smoothly the lighted columns at the pace of the light traveling from one column to the next. Each subject was subjected to 12 to 20 training trails at fixed velocity. The time gap, corresponding to this running velocity was well within the time range of visible persistence (32 milliseconds gap between successive presentations of a fragment on adjacent columns).

In order to pass the test phase it was required to demonstrate 90% correct identifications within 3 presentation cycles of each stimulus.

All subjects completed the training phase successfully within 15 minutes.

After this step the further step has been carried out.

b) Each subject was exposed to stimuli presented at 4 different time gaps. The term time gap in this context means the time interval (milliseconds) between the lighting of two adjacent columns, which run over the display. The stimuli were presented as 4 groups, having different list of words. Each list included eighteen words, consisted of 3 to 5 letters. All words were the most common in written Hebrew for school children.

The basic time gaps for the different lists were 58, 116, 232 and 464 milliseconds. Each list was displayed at one of the above time gaps at random for each subject. Single presentation order was used, i.e. from the shortest time gap to the longest.

Subjects' performance was recorded. When the rate of correct responses for a given list in a given time gap did not exceed 28%, the time gap was shortened in half of the distance between the failure time gap and the preceding one (e.g. failure in 232 milliseconds time gap and above criterion performance in 116 milliseconds led to a test with 174 milliseconds time gape).

A list of 18 stimuli (consisted of words taken from the original four lists) was used for the test in the intermediate time gap. This procedure was repeated if failure was recorded at the intermediate gap, till the above criterion level performance (28% of correct identifications) was reached.

Performance higher than the criterion level at the intermediate gap led to the increase of the time gap in half the distance between the intermediate gap and the preceding one were failure was inspected. This procedure was repeated till the first below criterion performance was recorded again. Distribution of failure time gaps in both samples (controls of age group 26-55 are not included) is presented in FIG. 1. It is evident from FIG. 1 that dyslexics fail at relatively shorter time gaps than the subjects of the control group.

Table 2 presents the average number of correct responses in the longest time gap where the subject performance was above the criterion level and the average correct responses in the failure time gap in both samples.

TABLE 2

|  | Average correct responses in failure time gap | Average correct responses (last success) |
|---|---|---|
| control (N = 510) | X = 2.78<br>SD = 0.89 | X = 16.70<br>SD = 1.64 |
| Dyslexics (N = 315) | X = 2.38<br>SD = 0.66 | X = 15.8<br>SD = 2.17 |

Table 2 indicates that the transition from success to failure is quite sharp and that within 20 to 30 ms time gap difference, performance may drop from 80%-100% correct responses to less than 20% correct responses.

EXPERIMENT 2

This experiment was intended to examine the effect of the present treatment method for improvement of attentive scanning upon reading performance of dyslexics.

Method:

Sixty male dyslexics of the former experiment that failed in time gaps of 126 to 184 milliseconds were the subjects of this experiment. This time gap range was chosen since within it as much as 38% of dyslexics failed while only 5% of controls. The 60 subjects were sampled in triplets according to age and time gap failure. This enabled the division of the sample to three groups.

One group used as the experimentally treated group (treatment group). The second was given an alternative reading training and the third group did not get any treatment (no-treatment group).

The Treatment Group

Each of the 20 subjects of this group was engaged with eight one-hour treatment sessions. In the first session the subjects were exposed to words and texts presented at time gaps of their last success in experiment 1. Gaining 90% or more correct responses led to the increase of the time gap in quarter (e.g. subject that performed successfully in time gap of 117 milliseconds were presented with stimuli at 146 milliseconds). The same stimuli were presented at the increased time gap. If performance level did not dropped, a new set of stimuli was presented at the same time gap. Time gap was increased again if performance level for the new set was within criterion level. If, during the next 15 minutes of testing, the performance was still below the criterion level the time gap was decreased in half of the difference between the last success and the testing gaps. This process continued until the end of the treatment sessions.

Alternative Reading Training Group

The 20 subjects of this group were given 8 thirty minutes treatment sessions of regular text reading. Each subject was presented with texts and words submitted to his yoked subject in the treatment group. The shorter treatment sessions in this group made more adequate the actual exposure time to texts as compared to the treatment group.

No Treatment Group

The subjects of this group were given the display test and the regular text reading tests but were not exposed to any treatment in between Testing sessions. On average, the time between initial and final testing in all groups was two and a half months.

Table 4 presents the vocal reading speed and error reading rate for standardized regular text before and after treatment.

TABLE 4

| Group | Reading speed (words/min) | | Error rate (%) | |
|---|---|---|---|---|
|  | Before | After | Before | After |
| Treatment | X = 74.6<br>SD = 26.4 | X = 87.3<br>SD = 19.9 | X = 11.20<br>SD = 5.70 | X = 4.10<br>SD = 2.80 |
| Alternative | X = 77.9<br>SD = 27.2 | X = 83.3<br>SD = 28.6 | X = 10.40<br>SD = 5.10 | X = 8.80<br>SD = 5.2 |
| No treatment | X = 72.8<br>SD = 23.7 | X = 74.5<br>SD = 25.0 | X = 13.2<br>SD = 6.6 | X = 12.9<br>SD = 6.2 |

Since the texts given were standardized fluency tests, the subjects' performance could be evaluated according to their standard scores. Table 5 presents these data.

TABLE 5

| Error rate | | Reading speed | | |
|---|---|---|---|---|
| Before | After | Before | After | |
| −0.69 | −2.58 | −1.43 | −1.83 | Treatment |
| 0.74 | 1.12 | 0.48 | 0.56 | |
| −2.06 | −2.32 | −1.60 | −1.69 | Placebo |
| 1.64 | 1.75 | 0.72 | 0.63 | |

TABLE 5-continued

| Error rate | | Reading speed | | |
| --- | --- | --- | --- | --- |
| Before | After | Before | After | |
| −3.11 | −3.22 | −1.46 | −1.90 | No treatment |
| 6.2 | 6.6 | 25.0 | 23.7 | |

These data show the advantage of the display treatment over spontaneous improvement and routine reading training in the subjects. The main effect appears in reading error rate decrease. In order to evaluate the improvement consistency within subjects, the difference of the fluency measures were calculated for each subject in each group. In 19 out of 20 subjects of the treatment group, a decrease of error rate was recorded as compared to 8 and 10 cases in the other groups. Table 6 presents the standard scores of the fluency measures for a novel text read only after the end of the treatment sessions.

TABLE 6

| Error Rate | Reading speed | |
| --- | --- | --- |
| 0.5 | −1.05 | Treatment |
| 0.62 | 0.86 | |
| 1.94 | −1.23 | Placebo |
| 1.43 | 1.0 | |
| −2.08 | −1.42 | No treatment |
| 1.03 | 0.93 | |

These data complies with the previous data as to the treatment effect on the reading error rate.

Clinical Observations and Post Hoc Analyses

Since most of the reading disabled participated in the above mentioned experiments were assessed by a cognitive battery intended for diagnosis of learning disabilities (Gordon et. al), it was of interest to examine weather their failure in the display test correlates with the performance on other cognitive tests.

In order to perform the correlations' inquiry, 116 files of subjects that failed in time gaps of 126 to 172 milliseconds were chosen (in that gap range only 2.9% of controls failed). The files of 116 matched reading disabled that performed normally on the display test were picked up too. Table 7 presents the distribution of the experimental group subjects according to age and gender.

TABLE 7

| 57 | 13 | 44 | 12-8 |
| --- | --- | --- | --- |
| 34 | 8 | 26 | 17-13 |
| 25 | 6 | 19 | 25-18 |
| 116 | 27 | 89 | Totals |

The performance of both groups on 27 different cognitive measures was examined. Four main tests were found to correlate with the display failure:

1. Point Location in Two-dimensional Space (Gordon).

The average standard score of those failed in the display test was far below normal score ($X=-1.6$, $SD=1.19$).

The matched reading disabled that performed normally on the display test was within the normal level ($X=0.56$, $SD=1.38$)

2. Digit—Symbol Test (Wecsler).

The average standard score of those failed in the display test was $X=7.64$, $SD=2.26$.

The average standard score of matched reading disabled was $X=8.40$, $SD=2.68$).

3. Digit—Logograph Test (Lamm).

The average standard score of those failed in the display test was $X=7.16$, $SD=2.33$.

The matched reading disabled standard score was $X=10.34$, $SD=3.06$.

4. Specific Graphic Characteristics in Writing to Standard Dictation (Lamm).

No standard scores are available for the evaluation of subjects' handwriting.

However it was clear that letters/words spacing and keeping parallel lines were much poorer in those subjects that failed in the display test.

The writing sheets of all subjects were evaluated by three independent observers, which were required to score each according to several criteria. It was found that the best differentiating criterion was letter and word spacing. Subjects that failed on the display test got average score of 3.9 ($SD=2.6$) on an 1 to 9 scale. Other reading disabled got 7.2 (2.0). Comparable normal readers received an average score of 8.4 (1.8).

Some other tests differentiate the groups in the reverse direction. That is, the display failures performed normally on these tests while the other reading disabled showed significantly inferior performance to norm level. Among these tests were free recall Word Dichotic Listening (Gordon) and the digit span (WISC-R/WAIS) test.

Background Differences.

The main background difference between the two groups of poor readers are related to diagnosis of ADHD. In the display failures, 46 subjects were recommended to be treated by stimulants following medical assessment. Other 28 were labeled as ADHD by psychologists or other professionals in the fields of child development. The background data from other disabled readers indicate that only 7 subjects were actually recommended to be treated by stimulants and other 19 were labeled as ADHD following psychological or other developmental assessment.

Thus it seems that the graphic display is most useful treatment device in cases of Dyslexia and ADHD comorbidity.

On the basis of the above-mentioned experiments the present method has been developed and can be used in clinical settings.

It is disclosed below how the present method can be used for treatment of school children and adults.

1. Training Step.

Subjects are presented with 15 initial training alphanumeric signs and words, presented each in a time gap of 80 milliseconds. These include all letter lines and angles used in the Hebrew alphabet. An example of the stimuli is shown in FIG. 2. Each stimulus is presented up to three times and subjects are instructed to name the presented stimulus. At this time gap all subjects identify all stimuli on the first to second presentation.

2. Test Step.

During this step the tested person who passed the first step is exposed to nine word groups each consisted of six words. These word groups are seen in FIGS. 3a,b,c. The groups are displayed at three different velocities, which correspond to the time gaps of 80, 144 and 180 milliseconds. All in all 18 words are presented in each velocity of which six are presented in all velocities. During each run the performance of the subject is recorded in terms of words correctly recognized from each group and at each velocity.

The subject performance is evaluated on the basis of correctly identified words. Prior data clearly indicate that normal readers can identify 16 to 18 stimuli out of the 18 presented stimuli in each time gap. This criterion, which is about 90% is the basis for subjects attribution either to those who suffer visual attention deficit or not. The common failure case takes place at the largest time gap. Most poor readers that fail in this velocity gain 0 to 5 correct responses Subjects that fail in the intermediate gap (0 to 14 correct responses) consistently demonstrate very poor performance on larger time gaps. No subject is expected to fail in the shortest time gap.

Thus, in most cases the results of this test are clear cut and thus the test is highly reliable in detecting the appropriate candidates for subsequent treatment in order to improve the visual attention deficit.

The same procedure is also available for pre-school children but, instead of alphanumeric signs, namable object pictures are presented.

3. Treatment Step.

The treatment step is based on a systematic variation of time gaps according to subjects' former performance. Subjects that failed on the test in 180 milliseconds gap but performed reasonably on 144 milliseconds gap. (16 to 18 correct responses) are presented with letters, words and sentences in intermediate gap (162 milliseconds. for this example). Successful performance (90% correct) leads to the enlargement of the time gap to intermediate time between 162 to 180 milliseconds. If, on the other hand the subject fails on 162 milliseconds gap he gets the help of the experimenter for 15 minutes in identifying the presented stimuli. If the subject himself within this time limit does not reach the criterion level, the time gap is shortened in half the gap between 162 to 144 milliseconds and the procedure is continued along the same lines. Improvement within 15 minutes leads to the use of new group of stimuli, never presented before, at the same time gap. If adequate performance for that group is gained, the time gap is increased in half the time distance between 162 to 180 milliseconds. If 90% correct responses are not recorded without assistance, the same group is used in a time gap, which is half of the distance between 144 and 162 milliseconds, i.e. 158 milliseconds The enlargement of time gap in the treatment sessions always follows after successful reading of a new list never seen before by the subject. The same list is used in the initial presentation at the enlarged gap. Shorting of the time gaps is always combined with the use of the last group of stimuli presented at the larger time gap.

The training sessions are continued until the performance level of 90% is reached for 240 milliseconds gap or until the end of the eight one-hour sessions. Most subjects reach this criterion level within 5 to 8 sessions. Others reach 90% correct responses rate for gaps, which are between 200 to 235 milliseconds. Only few subjects (17%) do not reach that level following eight sessions' training.

The same procedure can be also exploited for preschool children while specific object pictures instead of words are exposed on the visual display.

The present method can be implemented in any system, which comprises a graphic display and a control means. The display should be suitable for emulating stimuli and presenting them in a running mode, while the control means should be suitable for varying the parameters of the graphic display, e.g. time gaps, sequence of display, etc. As an example of suitable control means one can mention a PC, which communicates with the display and is configured to control the parameters of display, to record data, associated with the patient's performance and to analyze recorded data statistically. It should be appreciated that the present invention is not limited by the above-described embodiments and that one ordinarily skilled in the art can make changes and modifications without deviation from the scope of the invention as will be defined below in the appended claims.

For example instead of using graphic display, which is described above one can use other displays, e.g. screen of a TV set or even display, which can be worn on a patient's head as spectacles. Instead of using separate, dedicated display one can use control means, which has its own display, e.g. screen of a computer.

In the following claims the term comprising means "including but not limited to and the term visual attention deficit means deficit in processing fragmented visual stimuli as a whole due to short time gaps between presentations which are below the ability of human brain to detect such time intervals.

It should also be appreciated that features disclosed in the foregoing description, and/or in the foregoing drawings, and/or examples, and/or tables, and/or following claims both separately and in any combination thereof, are material for realizing the present invention in diverse forms thereof.

The invention claimed is:

1. A method for detection and improving of visual attention in a patient, said method comprising:
   a) generating of at least one group of visually recognizable stimuli, said stimuli being presented by alphanumeric signs displayed in a running mode defined by a time gap between consecutive stimuli;
   b) exposing the patient to the stimuli;
   c) determining the ability of the patient to recognize the stimuli;
   d) varying the time gap between the stimuli in accordance with the patient's ability to recognize the stimuli;
   e) a preliminary training step, in which the patient is exposed to a single group of stimuli displayed at an invariant time gap, which is set to match the within visual persistence frequency range limit of the human visual system of a normal person, who does not suffer from visual attention deficit;
   f) a diagnostic step, in which the patient is exposed to several consecutive groups of stimuli, which are displayed at least at a first and at a second time gap, said second time gap being larger than the first time gap and said diagnostic step results in establishing whether the patient suffers from visual attention deficit; and,
   g) a treatment step, in which the patient suffering from visual attention deficit is exposed to those groups of stimuli, which were displayed at the diagnostic step, but the patient recognized only part of the stimuli within a group, wherein the patient is exposed to a group containing unrecognized stimuli, which is displayed at an intermediate time gap, said intermediate time gap lies between the first time gap and the second time gap.

2. The method as defined in claim 1, in which said alphanumeric signs are emulated by virtue of lights of an array, in which said lights are arranged as a dot matrix.

3. The method as defined in claim 2, in which said lights are illuminated within the array to present a consequence of columns, said columns being fragments of stimuli, and said columns creating illusion of moving stimuli.

4. The method as defined in claim 1, in which said time gap is kept between 58 and 464 milliseconds.

5. The method as defined in claim 1, in which said alphanumeric signs are selected from the group consisting of letters and numbers.

6. The method as defined in claim 1, in which said stimuli are selected from the group consisting of letters, words, numbers and pictures.

7. The method as defined in claim 1, in which the single group displayed at the preliminary training step comprises 10-20 stimuli, which are letters, words and numbers and each group displayed at the diagnostic step comprises 6 stimuli, which are randomly selected words.

8. The method as defined in claim 1, in which the groups of stimuli displayed at the diagnostic step are not identical.

9. The method as defined in claim 1, in which during the diagnostic step the patient is exposed to 9 consecutive groups of stimuli, wherein each three groups are displayed at different time gaps.

10. The method as defined in claim 9, in which the consecutive groups are displayed at the time gap of 80, 144 and 180 milliseconds.

11. The method as defined in claim 1, in which establishing whether the patient suffers from visual attention deficit depends on the amount of stimuli correctly recognized by the patient at the diagnostic step.

12. The method as defined in claim 7, in which during the preliminary training step the single group of stimuli is displayed at least three times, each time at different time gap and during each time the amount of correctly recognized stimuli is recorded and the patient proceeds to the diagnostic step if he recognizes 90% of the stimuli.

13. The method as defined in claim 7, in which during the diagnostic step each group of stimuli is displayed at least three times, each time at different time gap and during each time the amount of correctly recognized stimuli is recorded.

14. The method as defined in claim 12, in which a patient is attributed as suffering from visual attention deficit when the amount of correctly recognized stimuli referring to the same group is less than 90%.

15. The method as defined in claim 11, in which during the treatment step the patient is exposed to consecutive groups of stimuli displayed at a first, second and third time gap, wherein the first time gap is shorter than the second time gap and the second time gap is shorter than the third time gap, wherein each time when the patient failed to recognize 90% of stimuli from a group displayed at the third time gap, but succeeded to recognize 90% of stimuli from a group displayed at the second time gap the patient is exposed to a group of stimuli displayed at an intermediate time gap, which lies between the third and the second time gap.

16. The method as defined in claim 15, in which each time when the patient failed to recognize 90% of stimuli from a group displayed at the intermediate time gap the patient is exposed to a group of stimuli displayed at a new time gap, which lies between the intermediate time gap and the second time gap and each time when the patient succeeded to recognize 90% of stimuli from a group displayed at the intermediate time gap the patient is exposed to a group of stimuli displayed at a new time gap, which lies between the intermediate time gap and the third time gap.

17. The method as defined in claim 16, in which the intermediate time gap is set to be an arithmetic average from the third time gap and the second time gap.

18. The method as defined in claim 17, in which the new time gap is set to be an arithmetic average from the intermediate time gap and the second time gap.

19. The method as defined in claim 17, in which the new time gap is set to be an arithmetic average from the intermediate time gap and the third time gap.

* * * * *